(12) United States Patent
Mercier et al.

(10) Patent No.: US 6,346,263 B1
(45) Date of Patent: Feb. 12, 2002

(54) BIODEGRADABLE IONIC MATRIX OF VARIABLE INTERNAL POLARITY WITH GRAFTED POLYMER

(75) Inventors: Philippe Mercier, Colomlers; Marianne Peyrot, Escalquens; Karim Ioualalen, Toulouse, all of (FR)

(73) Assignee: SARL Kappa Biotech, Montauban (FR)

( * ) Notice: Subject to any disclaimer, the term of this patent is extended or adjusted under 35 U.S.C. 154(b) by 0 days.

(21) Appl. No.: 09/269,499

(22) PCT Filed: Sep. 26, 1997

(86) PCT No.: PCT/FR97/01701

§ 371 Date: Mar. 14, 2000

§ 102(e) Date: Mar. 14, 2000

(87) PCT Pub. No.: WO98/13030

PCT Pub. Date: Apr. 2, 1998

(30) Foreign Application Priority Data

Sep. 27, 1996 (FR) .............................. 96 11978

(51) Int. Cl.⁷ .............................. A61F 2/00; A61K 9/14; A61K 47/30
(52) U.S. Cl. ...................... 424/426; 424/489; 514/772.3
(58) Field of Search .................. 424/1.1, 426, 489; 514/772.3

(56) References Cited

U.S. PATENT DOCUMENTS 5,151,264 A * 9/1992 Samain et al. ............... 424/1.1

FOREIGN PATENT DOCUMENTS

| DE | 44 28 851 | 2/1996 |
| WO | WO 92/06678 | 4/1992 |
| WO | WO 92/11871 | 7/1992 |
| WO | WO 94/20078 | 9/1994 |

OTHER PUBLICATIONS

By Y. Ohya et al., "Release behaviour of 5–fluorouracil from chitosan–gel microspheres immobilizing 5–fluorouracil derivative coated with polysaccharides and their cell specific recognition", *Journal of Microencapsulation*, vol. 10, No. 1, Feb. 1993, pp. 1–9.

* cited by examiner

*Primary Examiner*—Thurman K. Page
*Assistant Examiner*—Blessing Fubara
(74) *Attorney, Agent, or Firm*—Young & Thompson

(57) ABSTRACT

The present invention relates to a particulate biodegradable matrix comprising a biodegradable and hydrophilic core with a base of carbohydrate or polyol or polyamine matrix, cross-linked and derived in the mass by variable amounts of ionic groups; a hydrophilic polymer layer associated with the central core by chemical, for example ionic, interaction; and surface molecules or polymers grafted on the external polymer layer by covalent bonds.

10 Claims, No Drawings

BIODEGRADABLE IONIC MATRIX OF VARIABLE INTERNAL POLARITY WITH GRAFTED POLYMER

The present invention relates to a new type of biodegradable particulate matrix and the methods of its preparation.

Both in the fields of pharmacy and cosmetology, the use of numerous active principles remains sensitive and can be contemplated only for putting in place vectorization strategies. To cause a compound to penetrate and react in the interior of a biological or biochemical system, there exist a certain number of processes. It is however necessary to have a particulate vector in which the active principle is incorporated so as to be able to modify its behavior.

Thus the incorporation in a vector permits:
modifying the biodistribution of compounds having marked toxicity for a tissue
modifying the release mode and time of resonance at the site of administration and/or of action
improving the low solubility of certain molecules in physiological media
imparting a certain protection and increasing the half life of the molecule incorporated in the case of compounds having a too low half life in the organism or in the biological or biochemical systems.

The concept of vector must here by understood in the broad sense, which is to say that it comprises molecules playing a support role, for example when they are incorporated in a composition, either as such, or for the transport, presentation and/or stabilization of the active principle.

These strategies of vectorization are based on the use of particulate vectors obtained by techniques of solvent evaporation, polymerization in emulsion, or coacervation (patent WO 93.02712). These are the vectors based on polymers, polyamides, polypeptides, polyacrylates and derivatives, these are also the microparticles of peptidic origin, gelatins, alginates, polyamides obtained by gelification or by interfacial polymerization. All these techniques are well known to those skilled in the art. They are discussed in "Dossier Bioencapsulation, Biofutur, 1994 No. 132 p 1545". These vectors are for the most part difficult to be industrialized and remain troublesome. It must be emphasized that the techniques of evaporation lead to vectors containing traces of residual solvents and have for certain ones a toxicity which is not zero. Finally, there can be distinguished the liposomes widely used in cosmetology and for which the first pharmaceutical applications are arising but whose physico-chemical stability is still limited.

These different types of technologies have permitted obtaining several interesting results for solving certain problems of biodistribution and pharmacokinetics. Thus the forms of LHRH with timed release have been used as particles of polylactic/glycolic copolymer. Finally, the liposome forms of Doxorubicine, which are characterized by a modified biodistribution permitting avoiding the phenomenon of acute cardiotoxicity as described by "Bally et al. Cancer Chemotherapy and Pharmacology (1990) No. 27 p13–19" "Vaage et al, International Journal of Cancer (1992) No. 51 p 942–948". However, for numerous molecules, there exists no particulate vector having high capacity for incorporation, being modulable and easy to use industrially.

The ideal vector permitting the internal incorporation of molecules would have the following characteristics:
a particulate structure easily obtained without resort to conventional techniques difficult to employ, evaporation of solvent or gelification or interfacial covalent crosslinkage.
a high capacity for internal incorporation of molecules, followed by a high dispersability in aqueous media.
high stability of incorporation.
easy control and modulation of the release parameters.
ease of surface derivitization without risk of modification of the structure of the active principle.

Such a particulate vector must satisfy a certain number of requirements relating particularly to its useful load, its biocompatibility, its non-toxicity and its biodegradability. It must not upset the physiological equilibria and must not be immunogenic.

The only vectors which approximate this list of requirements are microparticles of copolymer of lactic/glycolic acid and the biodegradable ionic matrices.

The matrix of these microparticles is constituted by biodegradable polyesters of lactic acid and glycolic acid, two intermediaries of cellular metabolism. The speed of biodegradation is a maximum for a lactic/glycolic ratio of 1/1 by weight. These particular matrices are essentially prepared by the method known to those skilled in the art, so-called evaporation in solvent described in the patent "WO 93-02712", and by "BENOIT in New Pharmaceutical Forms. Technological, Biopharmaceutical and Medical Aspects, P. BURI et al editors, LAVOISIER Editions Tec and Doc 1985 page 632". To obtain an internal charge of the particle with this type of technology, it is necessary to incorporate the active principle with the polymer upon the initial dispersion phase in organic solvent. The solubility of the active principle in the organic solvent determines the maximum capacity of incorporation in the particle. This process implies the presence of the active principle throughout the process for synthesizing the particles, which is troublesome for radioactive and/or toxic products. For this type of vector, the release of the active principle depends on the speed of biodegradation of the particle and also on the properties of solubilization or diffusion of the molecule, hence on its physical condition.

In practice, for numerous molecules, speed of release is not constant with time and can be fairly long, which limits the use of this type of vector. As to the control of the size of the particles, this technology does not permit the industrial preparation of particles of a size below 200 nm, which considerably limits the therapeutic uses and particularly limits the possibilities of parenteral administration. Finally, those skilled in the art know that it is impossible, with this synthesis technique, totally to eliminate the residual traces of solvent, which remains problematic.

The biodegradable ionic matrices, also called ion exchange resins, are constituted by a three-dimensional network which is hydrophilic, swellable, not soluble in water and derived by an ion exchange capacity generally comprised between 0.1 and 10 mEq/g.

In particular, two families of resins can be distinguished: synthetic resins and resins obtained from natural and/or derived polymers.

The synthetic exchange resins are obtained by polymerization or copolymerization, in emulsion or reverse emulsion, of monomers comprising ionic functions, as described in the patent WO 93/07862. The natures of these resins as well as their size, porosity of ionic matrix, ion exchange capacity, rate of swelling, are controlled by different parameters of the synthesis process such as the quantity of water, the speed of agitation, and quantity and type of solvent, the quantity, type and concentration of the monomers. The monomers used at present are:
monoethylenic unsaturated monomers such as styrenes, styrene sulfanates, vinyl derivatives, acrylic and methacrylic esters. The monoethylenic unsaturated monomers with a protonic or basic function, include vinylpyridine and its derivatives, acrylate derivatives and methacrylate derivatives such as methacrylamidopropylhydroxyethyldimethylammonium acetate or chloride.

the unsaturated polyethylenic monomers include ethylene glycol diacrylates, ethylene glycol methacrylates, ethylene glycol or glycerol polyvinyls, divinylcetones, divinylsulfides, vinyl derivatives with carboxylate or sulfate functions, vinyl derivatives with pyridine or ammonium functions. However, the use of these polymers remains sensitive because of their limited or zero biodegradability. Finally, there cannot be totally eliminated, in the present state of the art, traces of residual solvents and of residual monomers, which can give rise to problems of toxicity.

The natural polymer resins are generally obtained from polysaccharides, naturally derived by ionic functions, for example chitosan, hyaluronic acids, alginates, carrogeeran. The technologies most often used are based on the functionalization and cross-linking of biodegradable polysaccharides, for example starch, cellulose or dextrin as described in French patent 75.17633. The matrices thus obtained have ion exchange capabilities comprised between 0.1 and 4 mEq/g. The great advantage of this type of polysaccharide matrix is its high capacity for incorporation of molecules associated with high biocompatibility and high biodegradability. It must nevertheless be noted that the internal incorporation of weakly hydrophilic compounds is very difficult with this type of matrix.

The present invention relates to a new type of biodegradable polymeric matrix adapted for the transport of molecules and characterized in that the polarity of the ionic matrix can be modified to permit the internal incorporation of hydrosoluble or hydrophobic molecules. The modification of the polarity and of the hydrophobic nature of the matrix is obtained by the derivation of the hydroxyl functions and/or by covalent grafting of weakly hydrosoluble radicals. This substitution, which takes place in a homogenous manner, can be introduced before, during or after cross-linking of the polymer. The properties of the matrix can therefore be modified by chemical coupling of weakly hydrosoluble or lipidic reagents, which is to say particularly fatty acids with saturated hydrocarbon chains, aliphatic straight or branched chains, and which comprise from 2 to 30 carbon atoms, preferably 2 to 12, sterols, fatty amines, hydrophobic aminated acids, alkoxyethers. If the reactions by grafting are well known to those skilled in the art, the process according to the invention involves an interesting modification in the manner of preferred use by carrying out a reaction in a protonic medium which is a solvent for the matrix but not a solvent for the lipidic molecules. This permits limiting the use of organic solvents usually used. It has been found that the reaction is preferably carried out in water, which permits maximum swelling of the matrix, with added acetic acid, of 0 to 60% or protonic acid of 0 to 10%. The derivation reagent is dispersed in the medium in the form of an emulsion with strong agitation at alkaline pH and low temperature to avoid hydrolysis of the reagent. This new process permits avoiding the use of conventional solvents for the polysaccharides and the fatty acids such as pyridine, which is known to those skilled in the art to be very difficult to eliminate, which can limit therapeutic applications. To maintain high biodegradability of the matrix, the different radicals are grafted preferably with help of labile bonds of the ester type.

These matrices are also characterized in that their surface can be derived in a non-covalent manner with polymers after internal loading of the molecules. The particle can thus acquire a new character connected to the physicochemical properties of the polymer grafted on the surface, for example bioadhesive or not being recognized by the reticuloendothelial system, or of tropism for a tissue or activation of the immune system.

Conferring a bioadhesive property permits increasing the dwelling time of the vector, hence of the active principle at the adsorption and/or action site. It also permits obtaining strict contact between the vector and the membrane and to localize the vector in particular mucous regions, of the selected tissues or organs. It is thus interesting for certain uses to use bioadhesive particles. Conventionally, the bioadhesive polymers used are of natural or semisynthetic origin and have numerous polar groups, a high molecular weight and a very flexible carbon skeleton as described by Junginger in Pharmaceutical Industry (1991) volume 53 No. 11 page 1056–1065. They are imbued with a high capacity for hydration. The polymers most often used are among others the polycarbophyls, alginates, polyacrylates, polyvinyl alcohols. These polymers can be grafted on the polysaccharide matrix by covalent chemical coupling reactions from hydroxyl groups well known to those skilled in the art. These are techniques based on the use of coupling agents such as epichlorhydrine or bifunctionals such as diepoxides, dialdehydes, dicarboxylates, diisothiocyanates. This can also be the carbodiamide technique for polymers having a carboxylate function. The matrices thus obtained are characterized by the presence of a peripheral layer of bioadhesive polymer of high molecular weight, from 6,000 to 50,000 daltons.

This grafting phase of a polymer at the surface cannot be carried out after the step of incorporation to avoid any risk of chemical modification of the active principle. The internal incorporation of molecules is thus conventionally carried out on matrices already provided with a polymeric covering which gives rise to numerous problems, because the polymers, among other things bioadhesive, can interact strongly with certain molecules, in particular the high molecular weight molecules, peptides and polypeptides, loaded molecules in general and prevent their incorporation in the matrix.

To avoid these difficulties, it is thus necessary to be able to graft the polymers after the incorporation of the molecules but without risk of chemical modification. The new technique developed according to the present invention is characterized in that the polymers are coupled to molecular species called macromolecules, permitting grafting on the loaded matrix, by coulomb interactions which are not susceptible to give rise to chemical modifications of the molecules of biological interest previously incorporated. These molecules are generally polymers of low molecular weight, biodegradable, of natural or synthetic origin, having numerous charges permitting anchoring by coulomb interactions on the ionic matrix of opposite charge. By macromolecules is principally intended the polysaccharides derived naturally by ionic functions, for example chitosan, hyaluronic acids, alginates, carrageeran, polypeptides or functional derivatives of polybiodegradable polysaccharides, for example starch, cellulose or dextran, the polyacidic polyglycolic derivatives such as derivatives of polyacrylates, polymethacrylates and polyphosphates and more generally polymeric macromolecules of a size comprised between 5,000 daltons and 50,000 daltons, of a capacity comprised between 0.2 and 15 mEq/g and having functions such as hydroxyls or amines, adapted to permit the establishment of covalent bonds with the polymer for example bioadhesive by simple chemical reactions.

The polymers can be grafted on a species called macromolecules, by covalent chemical coupling reactions, for example from hydroxyl groups of the polysaccharides well known to those skilled in the art. These are techniques based on the use of coupling agents such as epichlorhydrine or bifunctionals such as diepoxides, dialdehydes, dicarboxylates, diisothiocyanates. This can also be the carbodiimide technique for polymers having a carboxylate function.

More particularly, the present invention relates to a particularly useful matrix particularly for the transport of biologically active molecules.

These particles have a very high stability, a definite size which can be modulated as a function of the use by the choice of the cross-linked matrix and basically functionalized. They are adapted for the incorporation and transport or vectorization, of various synthetic, hemisynthetic, recombinant or natural molecules. These particulate matrices can be used to permit or increase the aqueous solubility and dispersability. They can also be used to obtain a modification of the release modes of the molecules with time, to include the physico-chemical stability of the sensitive molecules, to ensure the transport of the molecules into complex biological systems, eucaryotes or procaryotes, adapted to ensure chemical, photochemical, enzymatic, immunological reactions for pharmaceutical, cosmetological, diagnostic, study and research, and fermentation applications.

More particularly, the present invention relates to a particulate matrix characterized in that it comprises in this order, from the interior to the exterior, successively:

an internal ionic nucleus based on hydrates of carbon or reticulated polyols, hydrophilic, non-liquid and biodegradable, of adjustable internal polarity an internal hydrophilic polymeric layer, covering the central nucleus, with which it is associated by interactions of various natures, if desired ionic molecules or polymers with a surface grafted on the internal polymer layer by covalent bonds.

The central hydrophilic nucleus can be prepared by different methods well known to those skilled in the art. In particular, when there is a polysaccharide, preferably biodegradable, linear or branched, for example starch and their derivatives, cellulose, dextran, polysaccharides derived naturally by ionic functions, for example chitosan, hyaluronic acids, alginates, carrageeran, the ionic matrix is then obtained by reticulation and derivation by processes well known to those skilled in the art. The processes of reticulation can be carried out by the use of coupling agents adapted to react with the hydroxyl groups of the polysaccharides such as epichlorhydrine, epibromohydrine, bifunctionals such as diepoxides, dialdehydes, dichlorides of dicarboxylic acids, diisothicyanates, mixed anhydrides of carboxylic acids.

The ionic character of the matrix is obtained by using a polymer already derived from ion exchangers or by carrying out grafting on the neutral polymers of biocompatible and biodegradable ionic ligands, according to processes well known to those skilled in the art. The ionic ligands will preferably be selected from natural molecules present in the organism such as succinic acid, citric acid, phosphoric acid, glutanic acid, alanine, glycine. There are also used salts of glycidyl-trimethylammonium, salts of glycidyldimethylamine. Certain basic ligands such as 2(dimethylamino) ethanol, 2(diethylamino)ethylamine, 2(trimethylammonium)ethanol chloride, 3(trimethylammonium)propylamine, are grafted on the matrix by a bifunctional coupling agent adapted to establish an ester or amide linkage. There is preferably used for a coupling on the polysaccharide matrix succinic acid, phosphorus oxychloride, thiocyanates, diepoxydes. The grafting of the ion exchange functions can be carried out before, during or after the step of cross-linkage.

The ionized matrix can be obtained in the form of particles by several processes. The first consists in mechanically crushing the gel obtained by polymerization in mass. The second technique consists in producing the matrix directly in the form of particles by the technique of polymerization in dispersion in a liquid which is not miscible with the reaction phase.

These particles can be used for the administration of molecules by oral, lingual, nasa, vaginal, rectal, cutaneous, or ocular route, but also by a pulmonary and parenteral route. They can also be used for any topical application. These new vehicles for active principle are capable of encapsulating a large number of molecules with biological activity, such as:

peptides and their derivatives, glucagon, somatostatine, calcitonin, interferon and interleukines, LHRH, erythrpoieten, bradykinine antagonists, polypeptides such as recombinants derived from biotechnology antibodies proteoglycans anticancer agents antibiotics antivirals, in particular analogs of oligonucleotides and inhibitors of reverse transcriptase antiproteases insecticides and antifungals oligonucleotides, ADN and genome elements anesthetics and local anesthetics such as benzocaine vasoconstrictors cardiotonics such as digitoxin and digitalin and its derivatives vasodilators diuretics and antidiuretics neuroleptics antidepressants hormones and derivatives steroidal and non-steroidal anti-inflammatories antihistamines anti-allergic agents antiseptics diagnostic agents vitamins antioxidants amino acids and their mineral salts enzymes hydroxyacids and essential oils molecules with activity for the absorption of UV radiation or hydration of the skin.

Most of the molecules with biological activity can be incorporated, but also chromophore, fluorophore and/or radiolabelling agents. There can also be encapsulated animal and vegetable cells, such as bacteria, yeast and other microorganisms. The fields of use of these new particles are very wide not only for pharmaceutical, cosmetic and hygiene applications, but also for biotechnology, agro-food industry, diagnostics and the environment.

The present invention will be better understood, with its numerous advantages, by reference to the following particular cases, given by way of example, and which will in no way limit said invention. All the portions indicated in the examples are portions by volume and all the percentages are percentages by weight.

EXAMPLE 1 ACCORDING TO THE INVENTION

Preparation of Crosslinked and Cationic Polysaccharide Matrices

In a 2.5 liter reactor, there is introduced 100 grams of starch having a molecular weight of about 10,000, in 300 ml of water containing 1 gram of sodium borohydride. After 2 hours of stirring, there is added 100 ml of a 4N sodium hydroxide solution. When this solution is homogenous there are added 32 ml of an aqueous solution of 2,3-epoxypropyltrimethylammonium chloride, 75%. After 2 hours of agitation, there are added 7 ml of epichlorhydrin with continued agitation for 4 more hours. The solution is then let to stand for 40 hours. There is obtained a translucent brittle gel. This gel is taken up in 2 liters of water and the pH is adjusted to 5 by addition of 2N HCl. The gel is then washed four times with 5 liters of distilled water. There is obtained a matrix whose capacity, determined by titration, is 1 positive charge for 4 sugars.

EXAMPLE 2 ACCORDING TO THE INVENTION

Preparation of Cross-linked and Anionic Polysaccharide Matrices

In a 2.5 liter reactor, there is introduced 100 grams of starch having a molecular weight of about 10,000, in 300 ml of water containing 1 gram of sodium borohydride. After 2 hours of agitation, there are added 20 ml of a 0.2 N sodium hydroxide solution and the temperature is brought to −1° C. When the solution is homogenous, there is progressively added simultaneously 55 grams of succinic acid dichloride and 200 ml of a 4N sodium hydroxide solution, while maintaining the temperature at −1° C. After 4 hours of agitation, the pH is adjusted to 5 with the additional of 2N HCl. The gel is then washed by decantation 4 times in 5 liters of distilled water. There is thus obtained an anionic matrix cross-linked by the succinate whose capacity, determined by titration, is 1 negative charge for 4 sugars.

EXAMPLE 3 ACCORDING TO THE INVENTION

Preparation of Cross-linked Polysaccharide Matrices Functionalized with Phosphoric Acid In a 2.5 liter reactor, there is introduced 100 grams of starch having a molecular weight about 10,000, in 300 ml of 0.5 NaCl containing 1 gram of sodium borohydride. After 2 hours agitation, there is added 20 ml of a 4N sodium hydroxide solution and the temperature is brought to 3° C. When the solution is homogenous, there is progressively added at the same time 56 ml of phosphorus oxychloride and 500 ml of a 6N sodium hydroxide solution while maintaining the temperature at 3° C. After 4 hours of agitation, the solution is permitted to stand for 20 hours. There is obtained a translucent cross-linked gel. This gel is taken up in 2 liters of water and the pH is adjusted to 5 by addition of 2N HCl. The gel is then washed four times in 5 liters of distilled water. There is obtained an anionic matrix whose capacity, determined by titration, is 1 negative charge for 3 sugars.

EXAMPLE 4 ACCORDING TO THE INVENTION

Preparation of Cross-linked Polysaccharide Matrices Weakly Hydrophilic and Functionalized with Succinic Acid In a 2.5 liter reactor, 100 grams of starch is placed having a molecular weight about 10,000, in 300 ml of water containing 1 gram of sodium borohydride. After 2 hours of agitation, there is added 100 ml of a 4N solution of sodium hydroxide. When the solution is homogeneous, there is added 6 ml of epichlorhydrine while maintaining stirring for another 4 hours. The solution is then permitted to stand for 40 hours. There is obtained a translucent brittle gel. This gel is washed in 2 liters of water and the pH is adjusted to 6.8 by addition of 2N HCl. The gel is then recovered by decantation. The gel is then cooled to 0° C. and the pH is adjusted to 9 by a 0.2N solution of NaOH. Then under agitation, there is slowly added 60 ml of a solution of hexanoic acid chloride, 30%, into the propionic acid and the pH is maintained at 9, and then 30 grams of succinic anhydride. After the addition of the reagents, agitation is continued for 2 hours. The gel is then washed by decantation four times, in 2 liters of distilled water. There is obtained a weakly hydrophilic matrix derived with succinic acid, whose capacity, determined by titration, is 1 load for 8 sugars.

EXAMPLE 5 ACCORDING TO THE INVENTION

Preparation of Micromatrices by Pulverizing Cationic Matrices 100 grams of gel prepared according to Example 1, are taken up in 5 liters of water and pulverized with an Ultraturrax turbine for 7 minutes at 4000 rpm. The micromatrices obtained have a size comprised between 5 and 25 microns.

EXAMPLE 6 ACCORDING TO THE INVENTION

Preparation of Micromatrices by Pulverization of Anionic Matrices 100 grams of gel prepared according to Example 2 are taken up in 5 liters of water and crushed with the aid of an Ultraturrax turbine for 7 minutes at 4000 rpm. The micromatrices obtained have a size comprised between 15 and 50 microns.

EXAMPLE 7 ACCORDING TO THE INVENTION

Preparation of Micromatrices by a Combination of Matrices Ionized with Phosphate 100 grams of gel prepared according to Example 3 are taken up in 5 liters of water and crushed with an Ultraturrax turbine for 7 minutes at 4000 rpm. The obtained micromatrices have a size comprised between 0.5 and 5 microns.

EXAMPLE 8 ACCORDING TO THE INVENTION

Preparation of Micromatrices with Combination of the Matrices Derived and Ionized with Succinate 100 grams of gel prepared according to Example 4 are taken up in 5 liters of water and crushed with an Ultraturrax turbine for 7 minutes at 4000 rpm. The obtained micromatrices have a size comprised between 50 and 500 microns.

EXAMPLE 9 ACCORDING TO THE INVENTION

Preparation of Nanomatrices by Combination of Cationic Matrices 100 grams of gel prepared according to Example 1 are taken up in 10 liters of water and crushed with an Ultraturrax turbine for 3 minutes at 4000 rpm. This dispersion is then homogenized with a high pressure homogenizer of the Microfluidizer type at 1200 bars. The nanomatrices obtained have a size comprised between 50 and 150 microns.

EXAMPLE 10 ACCORDING TO THE INVENTION

Preparation of Nanomatrices by Combination of Anionic Matrices 100 grams of gel prepared according to Example 2 are taken up in 6 liters of water and crushed with an Ultraturrax turbine for 3 minutes at 4000 rpm. This dispersion is then homogenized with a high pressure homogenizer of the Microfluidizer type at 1000 bars. The nanomatrices obtained have a size comprised between 50 and 150 nanometers.

EXAMPLE 11 ACCORDING TO THE INVENTION

Preparation of Nanomatrices by Combination of Anionic Matrices 100 grams of gel prepared according to Example 3 are taken up in 8 liters of water and crushed with an Ultraturrax turbine for 3 minutes at 4000 rpm. This dispersion is then homogenized with a high pressure homogenizer of the Microfluidizer type at 1100 bars. The obtained nanomatrices have a size comprised between 50 and 150 nanometers.

EXAMPLE 12 ACCORDING TO THE INVENTION

Preparation of Nanomatrices by Combination of Anionic Matrices 100 grams of gel prepared according to Example 4 are taken up in 8 liters of water and crushed with an Ultraturrax turbine for 3 minutes at 4000 rpm. This dispersion is then homogenized with a high pressure homogenizer of the Microfluidizer type at 1200 bars. The nanomatrices obtained have a size comprised between 150 and 500 nanometers.

EXAMPLE 13 ACCORDING TO THE INVENTION

Preparation of Cationic Crosslinked Polysaccharide Matrices, by Crosslinking in Emulsion In a 2.5 liter reactor, there is introduced 100 grams of starch having a molecular weight about 10,000, in 300 ml of water containing 1 gram of sodium borohydride. After 2 hours of agitation, there is added 100 ml of a 4N solution of soda. When the solution is homogeneous, there is added 32 ml of a 75% aqueous solution of 2,3epoxypropyl trimethylammonium chloride. After 2 hours of agitation, there is added 5 ml of epichlorhydrine while continuing agitation. The solution is dispersed in 2 liters of dichloromethane under agitation sufficient to obtain the dispersion of the aqueous phase in the form of droplets of a size comprised between 50 and 500 microns. The dispersion is maintained under agitation at ambient temperature for 14 hours. The dispersion is then filtered and the spherical matrices taken up in 2 liters of 50% ethanol and the pH is adjusted to 5 by the addition of 2N HCl. It is then washed twice in 5 liters of 20% ethanol, then twice in 5 liters of distilled water, at 50° C.

EXAMPLE 14 ACCORDING TO THE INVENTION

Preparation of a Polymer Grafted on an Anionic Polysaccharide

In a 2.5 liter reactor, there is introduced 50 grams of starch having a molecular weight of about 10,000, in 200 ml of water containing 1 g of sodium borohydride. After 2 hours of agitation, there is added 100 ml of a 4N solution of sodium hydroxide. When the solution is homogenous, there is added 25 grams of succinic anhydride. After 2 hours of agitation, there is added 150 grams of 2,3epoxypropyl ether of hydroxypropylcellulose, and agitation is continued for 6 hours. The solution is then left to stand for 30 hours. A translucent gel is obtained. This gel is taken up in 2 liters of water and the pH is adjusted to 5 with the addition of 2N HCl. The gel is then washed 4 times in 5 liters of distilled water by ultrafiltration. There is obtained an anionic polysaccharide derived from dried hydroxypropylcellulose by lyophilization.

EXAMPLE 15 ACCORDING TO THE INVENTION

Ionic Anchoring of a Polymer Derived from an Anionic Polysaccharide on Cationic Matrices 50 grams of anionic micromatrices prepared according to Example 9 are dispersed in 250 ml of distilled water. At the same time, 10 grams of polymers derived from an anionic polysaccharide according to Example 14 are dispersed in 500 ml of distilled water. The dispersion of micromatrices is then added slowly with agitation to the bioadhesive polymer solution. After 2 hours of agitation, the matrices covered with polymer are recovered by decantation then washed twice with 2 liters of distilled water. There is thus obtained 54 grams of cationic matrices having bioadhesive properties.

EXAMPLE 16 ACCORDING TO THE INVENTION

Loading Oxytetracycline into Anionic Matrices

In a 1 liter reactor, 300 ml of a solution of oxytetracycline chlorohydrate, 10%, is slowly added and with agitation to 20 grams of polysaccharide matrix derived by the phosphate according to Example 3, in the form of a lyophilized dry substance. Agitation is maintained for 4 hours at ambient temperature. The matrices are then recovered by decantation, then washed four times with 500 ml of distilled water. There is recovered 28 grams of matrix loaded with 40% of oxytetracycline.

EXAMPLE 17 ACCORDING TO THE INVENTION

Loading Aspartic Acid into Cationic Matrices

In a 1 liter reactor, 10 grams of aspartic acid are mixed with 20 grams of polysaccharide matrix derived from the phosphate according to Example 3, in a dry lyophilized form. The mixture is slowly rehydrated with agitation by the addition of 400 ml of distilled water at ambient temperature. Agitation is maintained for 2 hours after complete rehydration. The particles of matrix are then recovered by decantation, then washed four times with 500 ml of distilled water. There is recovered 20 grams of matrix loaded with 20% of aspartic acid.

EXAMPLE 18 ACCORDING TO THE INVENTION

Preparation of Micromatrices Containing an Active Principle and Superficially Derived from a Bioadhesive Polymer The polymer prepared according to Example 14, is anchored on matrices prepared according to Example 16, by following the process described in Example 15.

What is claimed is:

1. Particulate biodegradable matrix comprising:
   a hydrophilic and biodegradable ionic nucleus based on a cross-linked matrix of carbohydrates or polyols or polyamines,
   a hydrophilic polymeric layer, associated with the nucleus by ionic chemical interactions,
   functional surface molecules or polymers grafted on the hydrophilic polymeric layer by covalent bonds.

2. The particulate biodegradable matrix according to claim 1, wherein the ionic nucleus is non-liquid and is grafted in the bulk of the core with lipophilic groups.

3. The particulate matrix according to claim 1, wherein acid compounds are grafted on the matrix.

4. The particulate matrix according to claim 1, wherein basic compounds are grafted on the matrix.

5. The matrix according to claim 2, wherein lipophilic groups selected from fatty acids, polyoxyethyleneglycols, fatty amines, hydrophobic aminated acids, sterols, alkoxyethers, and mixtures thereof are grafted on the ionic matrix.

6. The matrix according to claim 3, wherein the hydrophilic polymer layer is selected from natural and synthetic cationic polymers.

7. The particulate matrix according to claim 4, wherein the hydrophilic polymer layer is selected from natural and synthetic anionic polymers.

8. The matrix according to claim 1, wherein the surface polymers or molecules are bioadhesive or temporary relative to the reticuloendothelial system or have a tropism for a tissue or are activators of the immune system.

9. The matrix according to claim 1, further comprising a component with biological activity selected from:
   antibodies, proteoglycanes, anticancer agents, antibiotics, antivirals, analogs of oligonucleotides and inhibitors of reverse transcriptase, antiproteases, insecticides and antifungals, oligonucleotides, ADN and elements of the genome, anesthetics and local anesthetics, benzocaine, vasoconstrictors, cardiotonics, digitoxin and its derivatives, vasodilators, diuretics and antidiuretics, prostaglandines, neuroleptics, antidepressants, hormones and derivatives, steroidal and non-steroidal anti-inflammatories, antihistamines, anti-allergic agents, antiseptics, diagnostic agents, vitamins, antioxidants, aminated acids and mineral salts, enzymes, hydroxy acids and essential oils, animal and vegetable cells, yeast, bacteria, and other micro-organisms, and molecules with activity for the absorption of UV radiation or of hydrating the epidermis.

10. The matrix according to claim 1, wherein said matrix is marked by a chromophore agent or a fluorophore agent or a radioactive agent.

* * * * *